(12) United States Patent
Sastry et al.

(10) Patent No.: US 10,695,539 B2
(45) Date of Patent: Jun. 30, 2020

(54) DEVICE FOR MEASURING LENGTH OF TUBULAR BODY STRUCTURE

(71) Applicant: Myodynamics, LLC, Englewood Cliffs, NJ (US)

(72) Inventors: Ashwani Sastry, Englewood Cliffs, NJ (US); Sreejit Nair, Miami Lakes, FL (US)

(73) Assignee: MYODYNAMICS, LLC, Englewoods Cliffs, NJ (US)

( * ) Notice: Subject to any disclaimer, the term of this patent is extended or adjusted under 35 U.S.C. 154(b) by 721 days.

(21) Appl. No.: 15/469,121

(22) Filed: Mar. 24, 2017

(65) Prior Publication Data

US 2018/0271407 A1   Sep. 27, 2018

(51) Int. Cl.
| | | |
|---|---|---|
| *A61M 25/09* | (2006.01) | |
| *A61B 6/12* | (2006.01) | |
| *A61B 5/107* | (2006.01) | |
| *A61M 25/01* | (2006.01) | |
| *A61B 5/1495* | (2006.01) | |
| *A61B 5/06* | (2006.01) | |
| *A61B 5/00* | (2006.01) | |
| *A61B 6/00* | (2006.01) | |
| *A61M 25/00* | (2006.01) | |

(52) U.S. Cl.
CPC ............. *A61M 25/09* (2013.01); *A61B 5/064* (2013.01); *A61B 5/1076* (2013.01); *A61B 5/1495* (2013.01); *A61B 5/6853* (2013.01); *A61B 6/12* (2013.01); *A61B 6/487* (2013.01); *A61M 25/0108* (2013.01); *A61M 2025/0008* (2013.01)

(58) Field of Classification Search
CPC ..... A61B 5/6853; A61B 5/064; A61B 5/1495; A61B 5/1076; A61B 6/487; A61B 6/12; A61B 2025/0008; A61M 25/09; A61M 25/0108
See application file for complete search history.

(56) References Cited

U.S. PATENT DOCUMENTS

| | | | |
|---|---|---|---|
| 4,241,430 A | 12/1980 | Kayem et al. | |
| 5,092,561 A | 3/1992 | Moriuchi et al. | |
| 5,860,923 A * | 1/1999 | Lenker ............... | A61B 5/02014 600/433 |
| 6,954,991 B2 | 10/2005 | Akatsuka et al. | |
| 8,919,389 B2 | 12/2014 | Gries | |
| 2005/0050745 A1 | 3/2005 | Akatsuka et al. | |

(Continued)

*Primary Examiner* — Peter Luong
(74) *Attorney, Agent, or Firm* — Kanika Radhakrishnan; Evergreen Valley Law Group

(57) ABSTRACT

Disclosed is a device for measuring a length of a tubular body structure. The device comprises an elongated tubular member having a proximal end and a distal end. The elongated tubular member comprises a plurality of radiopaque markers uniformly arranged on the distal end and a plurality of non-radiopaque markers uniformly arranged on the proximal end. The elongated tubular member also comprises a guiding head member coupled to the distal end of the elongated tubular member. A number of the radiopaque markers of a portion of the distal end of the elongated tubular member conforming to an affected portion of the tubular body structure enables in measuring a length of the affected portion, when the elongated tubular member is inserted through a skin entry site of the tubular body structure under fluoroscopy.

27 Claims, 6 Drawing Sheets

(56) References Cited

U.S. PATENT DOCUMENTS

2013/0249139 A1 9/2013 Morita et al.
2013/0310645 A1* 11/2013 Desjardins ........... A61B 1/0125
                                              600/113

* cited by examiner

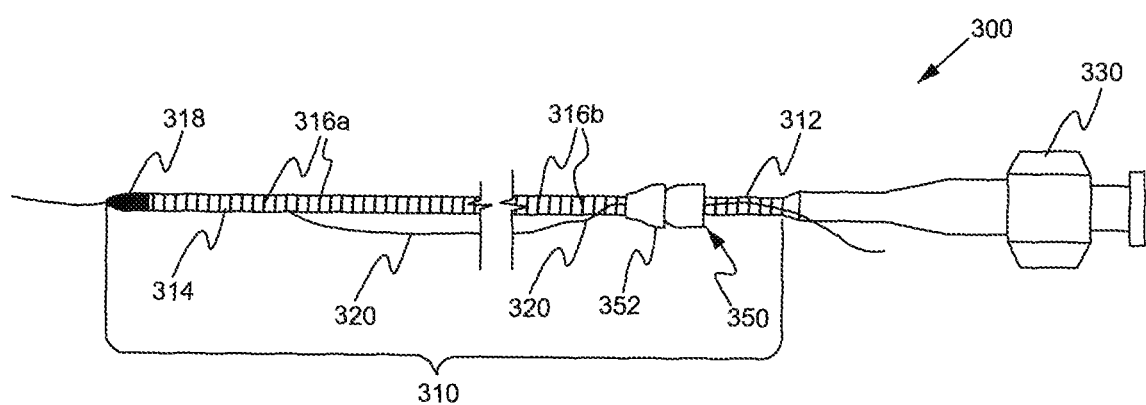
FIG. 3
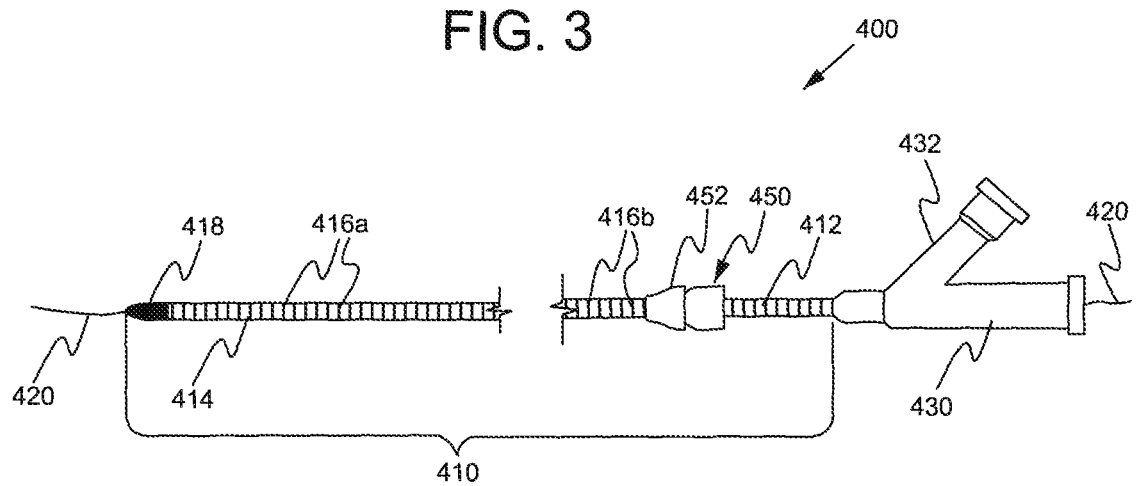
FIG. 4
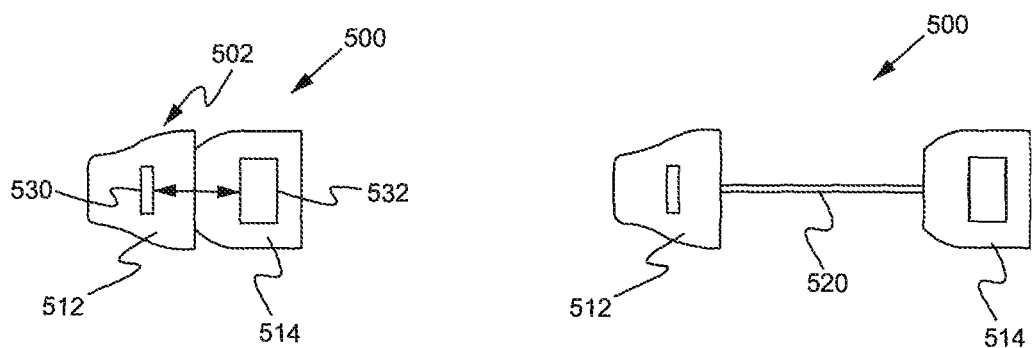
FIG. 5
FIG. 6

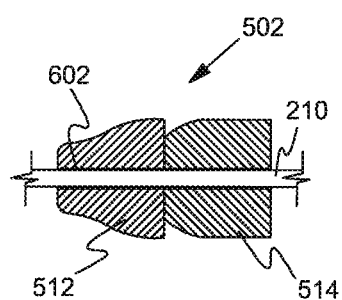 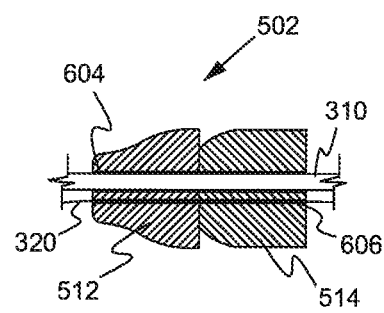 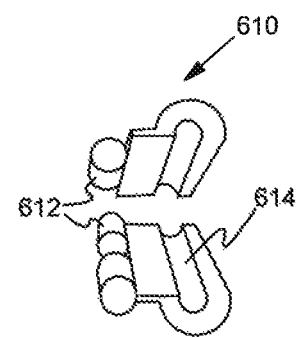
FIG. 6A  FIG. 6B  FIG. 6C
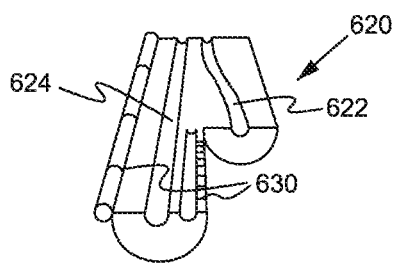
FIG. 6D
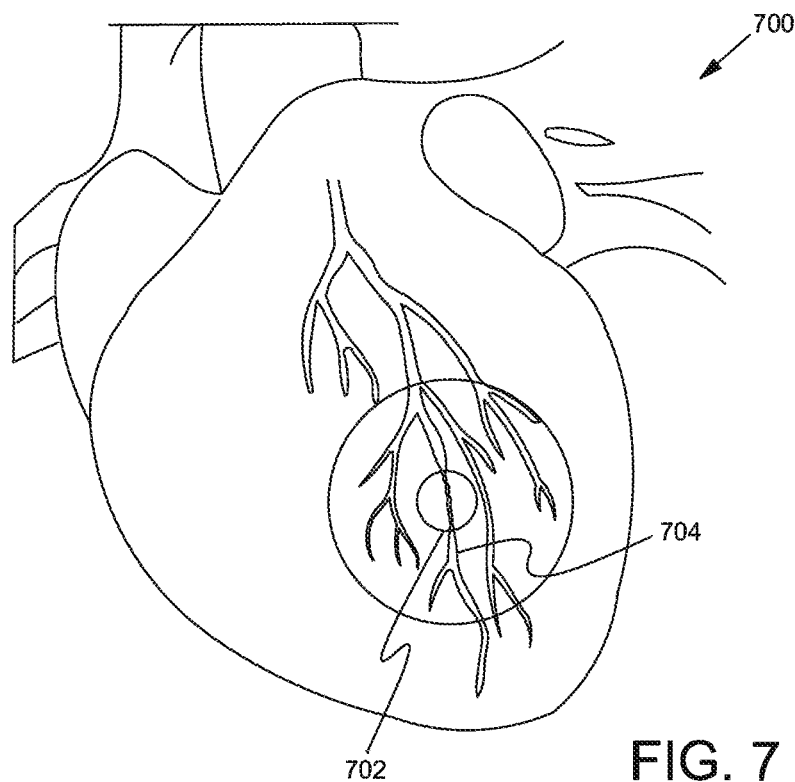
FIG. 7

DEVICE FOR MEASURING LENGTH OF TUBULAR BODY STRUCTURE

TECHNICAL FIELD

The present disclosure relates generally to medical devices, and more particularly, to a device for measuring a length of a tubular body structure.

BACKGROUND

Many medical procedures require length measurement of an affected or a diseased portion (such as a stenosis) of a tubular body structure (such as a blood vessel). Such measurements may be performed using quantitative angiography (QA), which uses software processing of acquired images. A known reference length on the image is provided as input to the software, and the operator marks a length of interest. Software processing of the image returns a length measurement. However, QA may not be always accurate due to complex imaging planes, curvature of vessels, and the need for calibration against a known length. Also, QA requires the physician to interrupt the procedure, adding to procedure time, and the software required for QA can be expensive.

An alternative method of length measurement involves the use of a catheter with evenly spaced radiographic markers. Such currently available catheters are 'over-the-wire' and can therefore be inconvenient to use in complex interventions. Further, as discussed in an US publication 20030088195 A1, a guide wire having measurement indicia, may address the above issue but this method restricts the physician to a specific type of guide wire. Typically, physicians like to choose guide wires based on their properties and the specifics of a procedure, and do not want to be limited to a particular guide wire that may not be ideal for the procedure. Additionally, markers on the guide wire decrease performance characteristics of the guide wire, and markers on the guide wire may be distracting for other critical parts of the procedure. Given the importance of precise length measurement with millimeter accuracy in many clinical applications, an independent mechanism for confirming (or authenticating) such length measurement is highly desirable.

In light of the foregoing discussion, there exists a need to overcome the aforementioned drawbacks of currently existing methods to measure lengths of tubular body structures in medical procedures.

SUMMARY

Various embodiments of the present disclosure provide a device, a length measuring arrangement, and a method of measuring the length of a tubular body structure.

In an embodiment, a device for measuring the length of a tubular body structure is disclosed. The device comprises an elongated tubular member having a proximal end and a distal end. The elongated tubular member comprises a plurality of radiopaque markers uniformly arranged on the distal end and a plurality of non-radiopaque markers uniformly arranged on the proximal end. The elongated tubular member also comprises a guiding head member coupled to the distal end of the elongated tubular member. A number of the radiopaque markers of a portion of the distal end of the elongated tubular member conforming to an affected portion of the tubular body structure enables in measuring a length of the affected portion, when the elongated tubular member is inserted through a skin entry site of the tubular body structure under fluoroscopy.

In an embodiment, a length measuring arrangement for a tubular body structure is disclosed. The length measuring arrangement is adapted to be mounted on an elongated tubular member having a proximal end, a distal end, a plurality of radiopaque markers uniformly arranged on the distal end, and a plurality of non-radiopaque markers uniformly arranged on the proximal end. The length measuring arrangement comprises a movable member; a sensor responsive to the non-radiopaque markers; and a processor communicably coupled to the sensor. The sensor and the processor are arranged on the movable member, and the sensor senses a number of the non-radiopaque markers on an extracorporeal segment of the elongated tubular member and the processor measures a length of an affected portion of the tubular body structure based on the sensed number of the non-radiopaque markers.

In an embodiment, a method for measuring a length of a tubular body structure is disclosed. The method comprises providing an elongated tubular member; the elongated tubular member comprises a proximal end, a distal end, a plurality of radiopaque markers uniformly arranged on the distal end and a plurality of non-radiopaque markers uniformly arranged on the proximal end. The method further comprises arranging a movable member on the proximal end of the elongated tubular member. The method also comprises inserting the elongated tubular member through a skin entry site of the tubular body structure, wherein the movable member is carried by an extracorporeal segment of the elongated tubular member. The method further comprises advancing the distal end of the elongated tubular member in a forward direction to pass through an affected portion of the tubular body structure, wherein the distal end of the elongated tubular member conforms to a distal end of the affected portion. The method also comprises moving the movable member to contact the skin entry site when the distal end of the elongated tubular member conforms to the distal end of the affected portion. The method further comprises determining a length of the affected portion of the tubular body structure by measuring a number of the radiopaque markers, under fluoroscopy on a portion of the distal end of the elongated tubular member, conforming to the affected portion. The method further comprises retreating the distal end of the elongated tubular member in a backward direction to pass through the affected portion and conform to a proximal end of the affected portion. The method further comprises confirming the determined length of the affected portion, by measuring a distance between the movable member and the skin entry site, which corresponds to a number of the non-radiopaque markers on the extracorporeal segment.

Other aspects and example embodiments are provided in the drawings and the detailed description that follows.

BRIEF DESCRIPTION OF THE FIGURES

For a more complete understanding of example embodiments of the present technology, reference is now made to the following descriptions taken in connection with the accompanying drawings in which:

FIGS. 1-4 are schematic illustrations of devices for measuring a length of a tubular body structure, in accordance with various example embodiments;

FIGS. 5-6 are schematic illustrations of a length measuring arrangement;

FIGS. 6A-6D are schematic illustrations of a movable member of the length measuring arrangement, in accordance with various example embodiments;

FIG. 7 is a schematic illustration of a heart having an affected portion along a tubular structure of the heart, in accordance with an example embodiment;

The drawings referred to in this description are not to be understood as being drawn to scale except if specifically noted, and such drawings are only exemplary in nature.

DETAILED DESCRIPTION

In the following description, for purposes of explanation, numerous specific details are set forth in order to provide a thorough understanding of the present disclosure. It will be apparent, however, to one skilled in the art that the present disclosure can be practiced without these specific details.

Reference in this specification to "one embodiment" or "an embodiment" means that a particular feature, structure, or characteristic described in connection with the embodiment is included in at least one embodiment of the present disclosure. The appearance of the phrase "in an embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

Moreover, although the following description contains many specifics for the purposes of illustration, anyone skilled in the art will appreciate that many variations and/or alterations to said details are within the scope of the present disclosure. Similarly, although many of the features of the present disclosure are described in terms of each other, or in conjunction with each other, one skilled in the art will appreciate that many of these features can be provided independently of other features. Accordingly, this description of the present disclosure is set forth without any loss of generality to, and without imposing limitations upon, the present disclosure.

Figure 1:
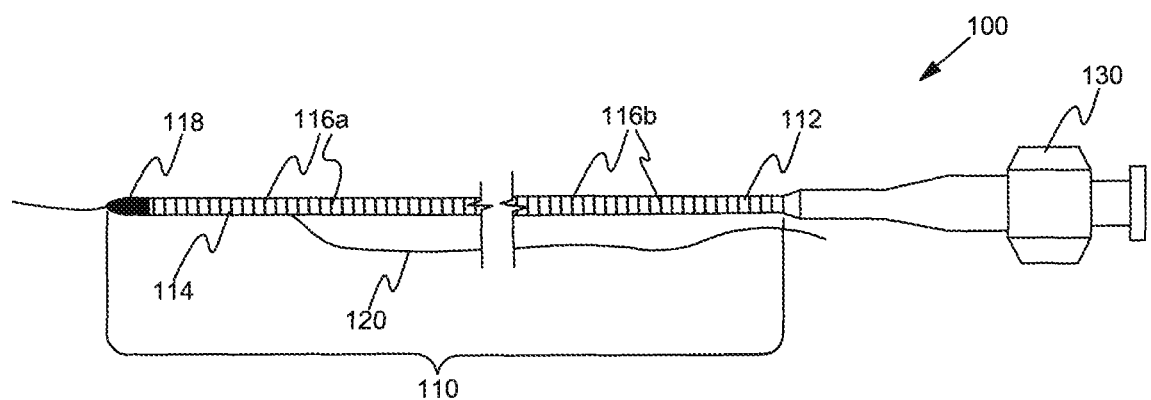

Referring now to the drawings, FIGS. 1-4 are schematic illustrations of devices for measuring a length of a tubular body structure, in accordance with various example embodiments. Specifically, FIG. 1 illustrates a device 100 for measuring a length of a tubular body structure. As shown, the device 100 includes an elongated tubular member 110 having a proximal end 112 and a distal end 114. The elongated tubular member 110 also includes a plurality of radiopaque markers 116a uniformly arranged on the distal end 114, and a plurality of non-radiopaque markers 116b uniformly arranged on the proximal end 112. The elongated tubular member 110 also includes a guiding head member 118 coupled to the distal end 114 of the elongated tubular member 110.

The device 100 is configured to accommodate a guide wire 120 of the user's choice, i.e. a medical practitioner handling the device 100 can select a guide wire based on his/her choice or comfort. The guide wire 120 is adapted to be received through the guiding head member 118 and extend out of the distal end 114. Specifically as shown, the guide wire 120 is received through the guiding head member 118 and exits from the distal end 114, passing alongside the elongated tubular member 110. As shown, it is to be understood that the elongated tubular member 110 is a mono-rail catheter, in accordance with the present embodiment. The elongated tubular member 110 may include a port 130 arranged at the proximal end 112 of the elongated tubular member 110 which communicates with the distal end 114, for embodiments in which the device 100 serves an angioplasty balloon catheter, delivery microcatheter, or drug delivery catheter, depending on the particular embodiment.

Figure 2:
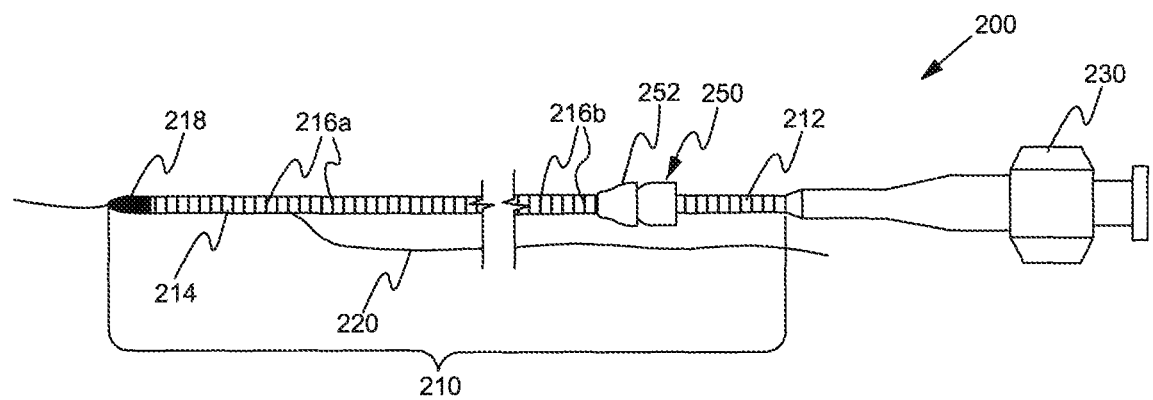

Referring now to FIG. 2, illustrated is a device 200 for measuring a length of a tubular body structure, in accordance with another example embodiment. The device 200 is similar to the device 100 of FIG. 1. For example, the device 200 also includes an elongated tubular member 210 having a proximal end 212, a distal end 214, a plurality of radiopaque markers 216a on the distal end 214, a plurality of non-radiopaque markers 216b on the proximal end 212, and a guiding head member 218. The device 200 also includes a guide wire 220. The elongated tubular member 210 may include a port 230 arranged at the proximal end 212 of the elongated tubular member 210 which communicates with the distal end 214, for embodiments in which the device 200 serves an angioplasty balloon catheter, delivery microcatheter, or drug delivery catheter, depending on the particular embodiment. However, the device 200 also includes a length measuring arrangement 250 mounted on the proximal end 212 of the elongated tubular member 210. The length measuring arrangement 250 includes a movable member 252, having a channel (not shown) conforming to a diameter of the elongated tubular member 210 to receive the elongated tubular member 210 there-through. The length measuring arrangement 250 will be explained in greater detail in conjunction with the subsequent figures. In one embodiment, the distal end 214 of the elongated tubular member 210 may include a single radiopaque marker, such as a radiopaque marker 216a, arranged at a tip of the guiding head member 218. Such single radiopaque marker along with the length measuring arrangement 250 may enable in measuring a length of the affected portion, which will be understood in conjunction with subsequent figures.

Referring now to FIG. 3, illustrated is a device 300 for measuring a length of a tubular body structure, in accordance with another example embodiment. The device 300 is similar to the device 200 of FIG. 2. For example, the device 300 includes an elongated tubular member 310 having a proximal end 312, a distal end 314, a plurality of radiopaque markers 316a on distal end, a plurality of non-radiopaque markers 316b on proximal end, and a guiding head member 318. The device 300 also includes a guide wire 320 and a port 330. The port 330 is arranged at the proximal end 312 of the elongated tubular member 310 which communicates with the distal end 314, for embodiments in which the device 300 serves an angioplasty balloon catheter, delivery microcatheter, or drug delivery catheter, depending on the particular embodiment. The device 300 also includes a length measuring arrangement 350 having a movable member 352. However, the length measuring arrangement 350 is mounted on the proximal end 312 of the elongated tubular member 310 and also configured to receive the guide wire 320 there-through. For example, the guide wire 320 (along with the elongated tubular member 310) is configured to be received through a channel (not shown) in length measuring arrangement 350. In one embodiment, the distal end 314 of the elongated tubular member 310 may include a single radiopaque marker, such as a radiopaque marker 316a, arranged at a tip of the guiding head member 318. Such single radiopaque marker along with the length measuring arrangement 350 may enable in measuring a length of the affected portion, which will be understood in conjunction with subsequent figures.

FIG. 4 illustrates a device 400 for measuring a length of a tubular body structure, in accordance with yet another example embodiment. The device 400 is similar to the device 200 of FIG. 2. For example, the device 400 also includes an elongated tubular member 410 having a proximal end 412, a distal end 414, a plurality of radiopaque markers 416a, a plurality of non-radiopaque markers 416b, and a guiding head member 418. The device 400 also includes a guide wire 420; however the guide wire 420 passes through an entire length of elongated tubular member 410 from the proximal end 412 to the distal end 414. Specifically, the elongated tubular member 410 includes separate a port 430 arranged on the proximal end 412 and adapted to receive the guide wire 420 there-through and along the entire length of the elongated tubular member 410. The elongated tubular member 410 also can include a separate port 432 arranged on the proximal end 412. The port 432 may be used for inflation, drug delivery and so forth, depending on the type of device 400, i.e. being an angioplasty balloon catheter, delivery microcatheter, or drug delivery catheter, and the like. As shown, it is to be understood that the elongated tubular member 410 is an over-the-wire catheter, in accordance with the present embodiment. The device 400 also includes a length measuring arrangement 450, having a movable member 452, mounted on the proximal end 412 of the elongated tubular member 410.

Referring now to FIGS. 5-6, illustrated is a length measuring arrangement 500 (such as the length measuring arrangements 250, 350, 450 of the devices 200, 300, 400 of FIGS. 2-4), in accordance with various example embodiments. As shown, the length measuring arrangement 500 includes a movable member 502. In one embodiment, the movable member 502 includes a first movable part 512 and a second movable part 514. In one embodiment, the first movable part 512 and the second movable part 514 may not be retractably coupled to each other. Further, in one embodiment, the movable member 502 may include a single movable part (or may be a monolithic structure). As shown in FIG. 6, the first movable part 512 and the second movable part 514 are retractably coupled to each other using a retractable member 520. According to an embodiment, the retractable member 520 may be one of an elastic member made of rubber, a metallic spring and so forth.

As mentioned herein above, the length measuring arrangement 500 may be carried by an elongated tubular member (such as the elongated tubular member 210) or may accommodate a guide wire (such as the guide wire 320). In an example embodiment, the movable member 502 (i.e. the first and second movable parts 512, 514) may include a channel conforming to a diameter of the elongated tubular member. Specifically, as shown in FIG. 6A, the movable member 502 (i.e. the first and second movable parts 512, 514) includes a channel 602 running along the first and second movable parts 512, 514, and the channel 602 is configured to conform to an elongated tubular member, such as the elongated tubular member 210. It may be evident that such a configuration of the movable member 502 may be applicable for the device 200, shown and explained in conjunction with FIG. 2.

Alternatively, the movable member 502 (i.e. the first and second movable parts 512, 514) may include separate channels conforming to diameters of an elongated tubular member (such as the elongated tubular member 310) and a guide wire (such as guide wire 320). Specifically, as shown in FIG. 6B, the movable member 502 (i.e. the first and second movable parts 512, 514) includes channels 604 and 606 running along the first and second movable parts 512, 514, and having diameters configured to conform to diameters of the elongated tubular member, such as the elongated tubular member 310, and the guide wire, such as the guide wire 320. It may be evident that, such a configuration of the movable member 502 may be applicable for the device 300, shown and explained in conjunction with FIG. 3. The movable member 502 shown in FIG. 6 may enable in keeping the guide wire 320 in a fixed position while the user pulls back the elongated tubular member 310. Therefore, such arrangement keeps the guide wire 320 away from entangling with the elongated tubular member 310, and avoids the guide wire 320 from being bent.

Additionally, the movable member 502 may be configured to have a common channel for the elongated tubular member and the guide wire. For example, as shown in FIG. 6A, the movable member 502 may include a channel to receive the elongated tubular member therethrough, and the elongated tubular member is adapted to receive a guide wire there-through along the entire length of the elongated tubular member.

In one embodiment, the movable member 502 is removably mounted on the proximal end of the elongated tubular member (or the guide wire). For example, the movable member 502 may be snap-fitted on the proximal end of the elongated tubular member (and the guide wire). Alternatively, the movable member 502 may be only removably mounted on a guide wire (not shown). In such instance, the movable member 502 may include a lone channel to receive the guide wire therethrough.

In one embodiment, a movable member may include a hinge and channels (or cutouts) along a length thereof, and the movable member may be opened along the hinge and channels being snap-fitted onto the elongated tubular member and the guide wire. As shown in FIG. 6C, a movable member 610 includes a hinge 612 and a channel 614 along a length thereof, and the movable member may be opened along the hinge 612 and channel 614 may be snap-fitted onto an elongated tubular member (not shown) and a guide wire (not shown).

In one embodiment, the movable member may include a hinge and channels (or cutouts) along a length thereof, and the movable member may be opened along the hinge and channels being snap-fitted onto the elongated tubular member and the guide wire. As shown in FIG. 6C, a movable member 610 includes a hinge 612 and a channel 614 along a length thereof, and the movable member may be opened along the hinge 612 and channel 614 may be snap-fitted onto an elongated tubular member (not shown) and a guide wire (not shown). Furthermore, referring now to FIG. 6D, illustrated is a moveable member 620, particularly one half thereof. The moveable member 620 includes channels 622, 624 for receiving an elongated tubular member and a guide wire, respectively, therethrough. The moveable member 620 includes markings at regular intervals, such ruler 630, which allow measurement of distance of pullback visually by examination of distance along the moveable member 620.

Alternatively, the movable member 502 may be mounted onto the proximal end of the elongated tubular member (and/or guide wire) via a sliding mechanism. Further, the movable member 502 may be mounted on the proximal end of the elongated tubular member by a threading/screw mechanism. Specifically, the movable member 502, and the proximal end of the elongated tubular member may include complimentary threads to enable threaded coupling.

Referring back to FIG. 5, the length measuring arrangement 500 further includes a sensor 530 responsive to the non-radiopaque markers and a processor 532 operatively coupled to the sensor 530. The sensor 530 and the processor 532 are arranged on the movable member 502. As shown, the sensor 530 is arranged on the first movable part 512 and the processor 532 is arranged on the second movable part 514. Alternatively, when the movable member 502 may be a single movable part the sensor 530 and processor 532 may be carried by such single movable part.

Further, the non-radiopaque markers on the proximal end of the elongated tubular member may be different from the markers on the distal end of the elongated tubular member. For example, the non-radiopaque markers on the proximal end of the elongated tubular member may be optical markers or mechanical markers (mechanically etched marks, visually painted lines, and so forth). Therefore, the sensor 530 may be an optical sensor responsive to the optical markers. Further, the sensor 530 may be responsive to the mechanical markers. For example, when the sensor 530 moves over such non-radiopaque markers the sensor 530 can sense the number of non-radiopaque markers and the processor 532 can count the sensed number of non-radiopaque markers. Alternatively, in case of mechanical markers, such markers may be simply read without the help of the sensor 530. Moreover, the markers may be uniformly spaced apart from each other for example in a range of millimeters (mm) or centimeters (cm).

In one embodiment, the elongated tubular member may include radiopaque markers along an entire length of the elongated tubular member, i.e. from the proximal end of the elongated tubular member to the distal end of the elongated tubular member. It is to be understood that, in such instance the sensor may be responsive to the radiopaque markers.

Referring now to FIG. 7, illustrated is a schematic illustration of a heart 700 having an affected portion 702 along a tubular body structure 704 (such as a blood vessel for example coronary artery) of the heart 700, in accordance with an example embodiment. The affected portion 702 may be a lesion, i.e. a region in an organ or tissue, which has suffered damage through injury or disease, such as a wound, ulcer, abscess, or tumor. In one embodiment, the affected portion 702 (or lesion) may be associated with tubular body structures associated with other body organs, for example, may be a blood vessel of limbs or tubular body structures of a digestive system or a respiratory system and so forth. The devices 100-400 of the present disclosure enable in measuring precisely a length (or lengths) of the affected portion 702, which will be explained in greater detail in conjunction with FIGS. 8A-8D.

Figure 8A:
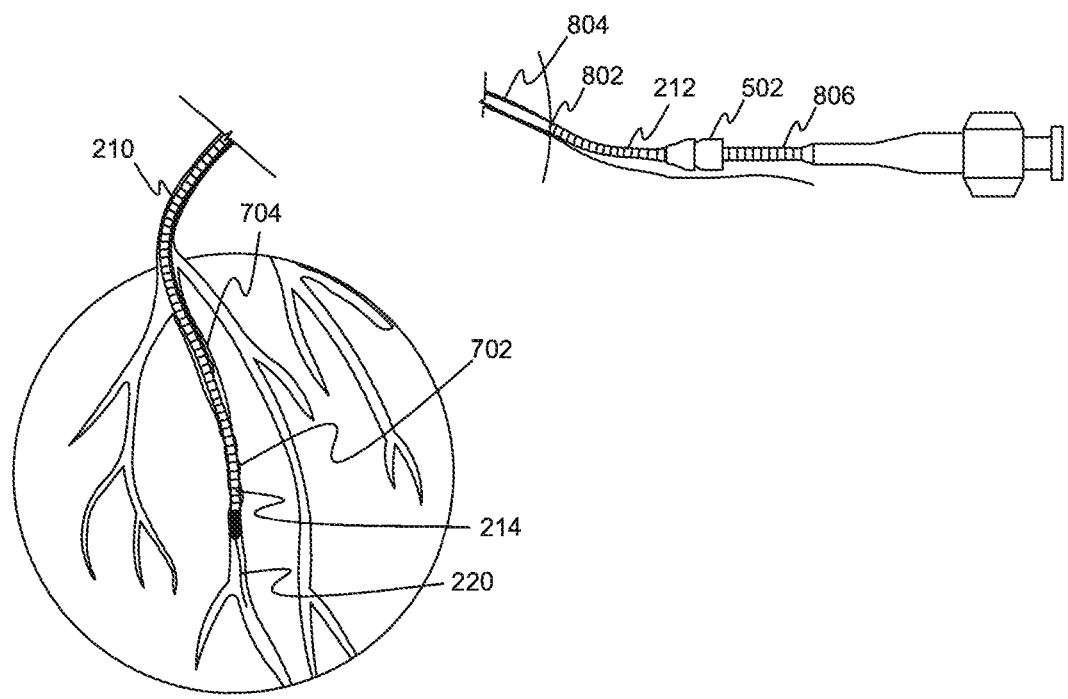
FIG. 8A-8D are schematic illustrations of various operational stages involved in measuring a length of a tubular body structure using a device, in accordance with an example embodiment.

Referring to FIG. 8A-8D illustrated are various operational stages involved in measuring a length of a tubular body structure using a device (such as the device 200), in accordance with an example embodiment. Specifically, as shown in FIG. 8A, the elongated tubular member 210 and the guide wire 220 are inserted through a skin entry site 802. However, it may be evident to those skilled in the art that the elongated tubular member 210 and the guide wire 220 may be inserted through a guide sheath (or guide catheter) into a tubular body structure 804 (for example a femoral artery). The elongated tubular member 210 and the guide wire 220 may be inserted into the skin entry site 802 using a guide catheter (not shown) or a sheath and so forth. Further, the movable member 502 is carried by an extracorporeal segment 806 (i.e. on proximal end 212) of the elongated tubular member 210. Moreover, the distal end 214 of the elongated tubular member 210 and the guide wire 220 are shown to pass through the affected portion 702 of the tubular body structure 704 (such as the coronary artery). It is to be understood that, the procedure shown in this FIG. 8A-8D may be associated with precise measurement of the length (or depth) of the affected portion 702 for the purposes of stent length, balloon length and so forth.

Figure 8B:
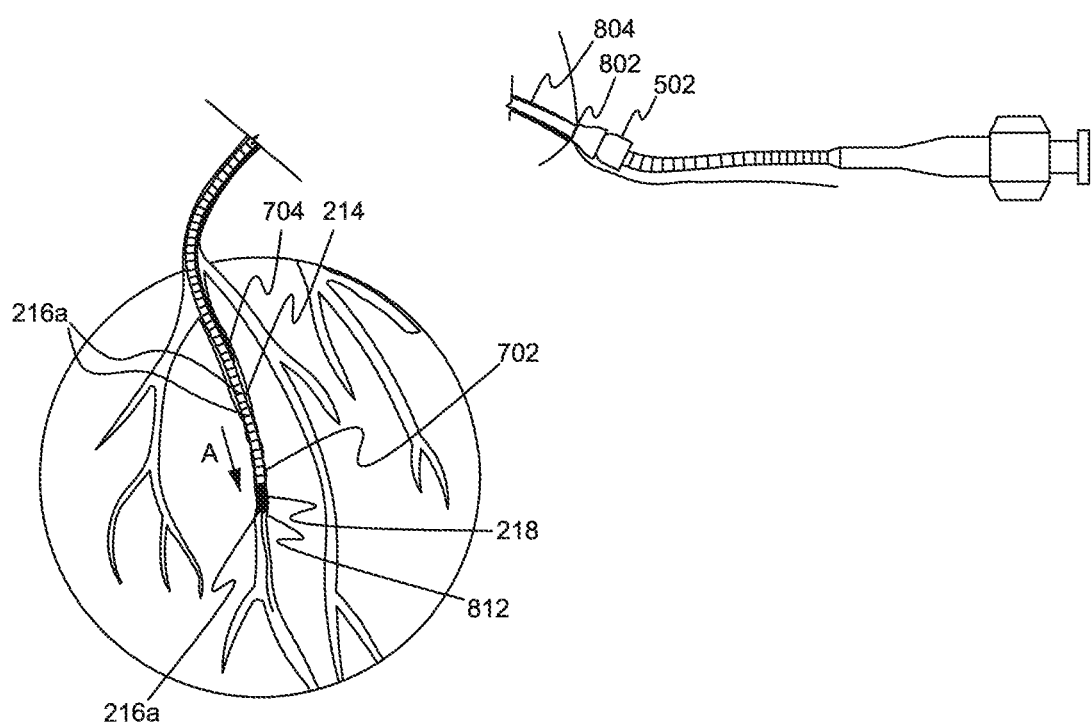

FIG. 8B shows that the guiding head member 218 of the elongated tubular member 210 is operable to pass through the affected portion 702 of the tubular body structure 704 in a forward direction (shown with arrow A) to conform to a distal end 812 of the affected portion 702. Specifically, the guiding head member 218 of the elongated tubular member 210 is adjusted (moved forward and/or backward) to conform (or align) with the distal end 812 of the affected portion 702. This may be done by seeing radiopaque markers 216a on the distal end 214 (and/or on the guiding head member 218) under fluoroscopy. Further, FIG. 8B also illustrates the movable member 502 being moved to contact the skin entry site 802 (or guide sheath or guide catheter) of the tubular body structure 804 when the guiding head member 218 conforms to the distal end 812 of the affected portion 702.

Figure 8C:
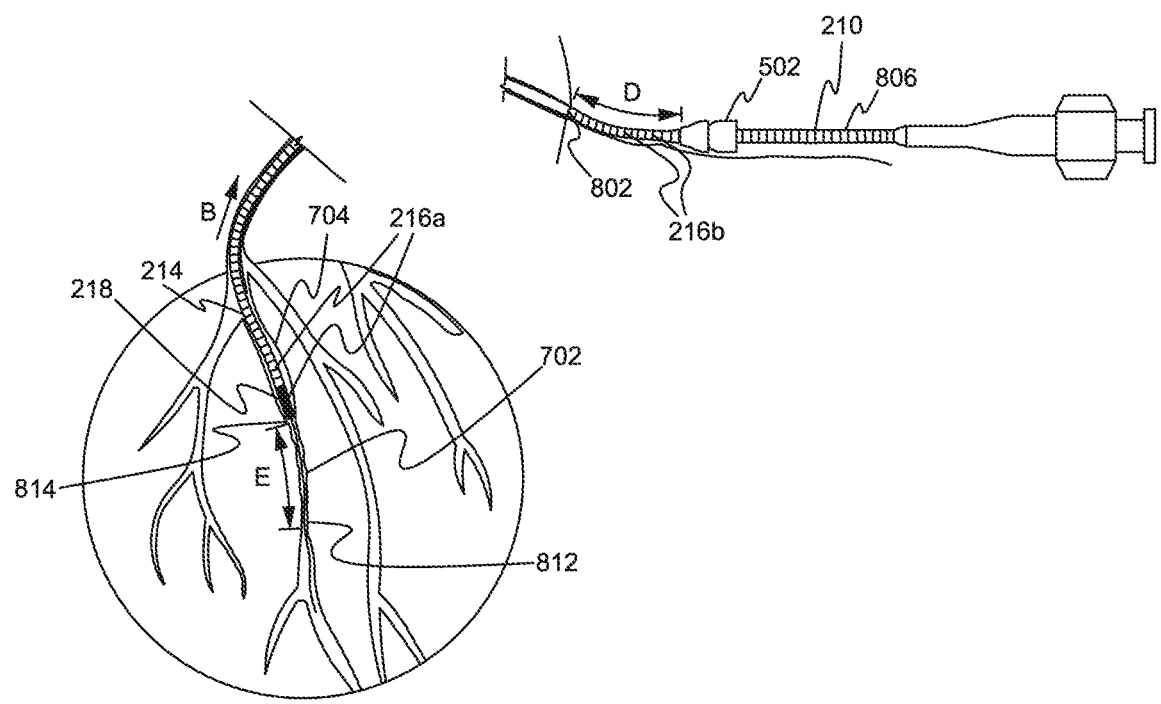

Referring to FIG. 8C, illustrated is the movable member 502 retained in a fixed position and the guiding head member 218 is retreated in a backward direction (shown with arrow B) to pass through the affected portion 702 and conform to a proximal end 814 of the affected portion 702. This may be done by seeing radiopaque markers 216a on the distal end 214 (and/or the guiding head member 218) under fluoroscopy. Therefore, a distance 'D' between the movable member 502 and the skin entry site 802 (or guide sheath or guide catheter) is determined to measure a length of the affected portion 702 of the tubular body structure 704. The distance 'D' between the movable member 502 and the skin entry site 802 equals distance 'E' between the distal and proximal ends 812, 814 of the affected portion 702. Therefore, it may be evident that a number of the non-radiopaque markers 216b on the extracorporeal segment 806 of the elongated tubular member 210 enables in measuring and authenticating the measured length 'E' of the affected portion 702 of the tubular body structure 804. Accordingly, the distance 'D' between the skin entry site 802 (or guide sheath or guide catheter) and the movable member 502 on the extracorporeal segment 806 of the elongated tubular member 210 enables in measuring and authenticating the measured length 'E' of the affected portion 702 of the tubular body structure 804.

Figure 8D:
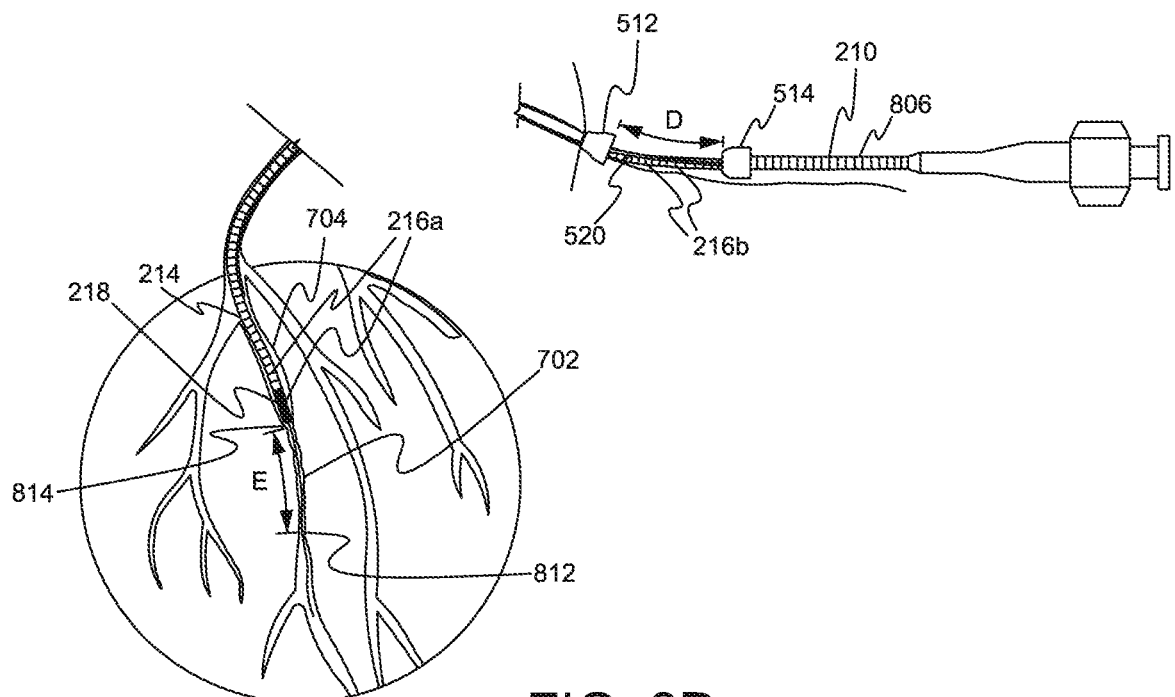

As shown in FIG. 8D, the distance 'D' between the first movable part 512 and the second movable part 514 (retractably coupled to each other using the retractable member 520) of the movable member 502 may be measured for measuring and authenticating the measured length 'E' of the affected portion 702 of the tubular body structure 804. Specifically, the sensor 530 (shown in FIG. 5) senses a number of the non-radiopaque markers 216b and the processor 532 measures the length 'E' of the affected portion 702 by measuring the distance 'D' based on the sensed number of the non-radiopaque markers 216b on the extracorporeal segment 806. In an example, if the sensor 530 senses 10 radiopaque markers, spaced apart by 1 mm, then processor 532 measures the length 'E' being 10 mm. It is to be understood that, the processor 532 may include algorithms to perform such calculation. In one embodiment, the length measuring arrangement 500 may include a method for normalization or zeroing, such that once the length measuring arrangement 500 is zeroed, movements (either in one direction or in both directions) are recorded, until the length measuring arrangement 500 is again zeroed. For example, the movements of the distal end 214 of the elongated tubular member 210 will be tracked 1:1 with movement of the moveable member 502, which is mounted on the extracorporeal segment 806. Similarly, placing the distal end 214 of the elongated tubular member 210 at the distal end 812 of the affected portion 702 (or region of interest) and subsequently retreating the distal end 214 of the elongated tubular member 210 in a backward direction to pass through the affected portion 702 and conform to a proximal end 814 of the affected portion 702 will allow measurement of the length of interest 'D' by means of 1:1 movements of the moveable member 502 on the extracorporeal segment 806. Additionally, the length measuring arrangement 500 may include a display configured on the movable member 502 for displaying such measured length 'E'.

In one embodiment, a back end (i.e. the second movable part 514) of the movable member 502 may be coupled to the elongated tubular member via a screw mechanism, and a front end (i.e. the first movable part 512) may be affixed to the sheath or guide catheter via a screw mechanism. In such instance, the length measurement would be determined by the retractable member 520 connecting the two parts of the movable member 502. For example, the retractable member 520 may include measurement markers on it, which may enable in length measurement. Alternatively, the retractable member 520 may be provided with a sensor operable to sense a length of extension of the retractable member 520, and the processor 532 may be operable to process such sensed length to provide the measured length.

Further, the device 300 (shown in FIG. 3) may follow the similar operational stages, depicted in FIGS. 8A-8D, for measuring a length of a tubular body structure using a device 300. However, the length measuring arrangement 350 is mounted on both the elongated tubular member 310 the guide wire 320 for measuring a length of an affected portion of a tubular body structure. Further, the device 400 (i.e. in which the elongated tubular member 410 is over-the-wire catheter) may follow the similar operational stages, depicted in FIGS. 8A-D, for measuring a length of an affected portion of a tubular body structure. Finally, for the device 100 (of FIG. 1), which lacks length measuring arrangement, counting under fluoroscopy the number of radiopaque markers 116a on the distal end of the elongated tubular member that span an affected portion of the tubular body structure allows length measurement. This measurement can be confirmed by pullback as in FIGS. 8A-8D, with distance D determined by visually counting the number of non-radiopaque markers (in this case, markers visible to the naked eye) that span length D.

Figure 9:
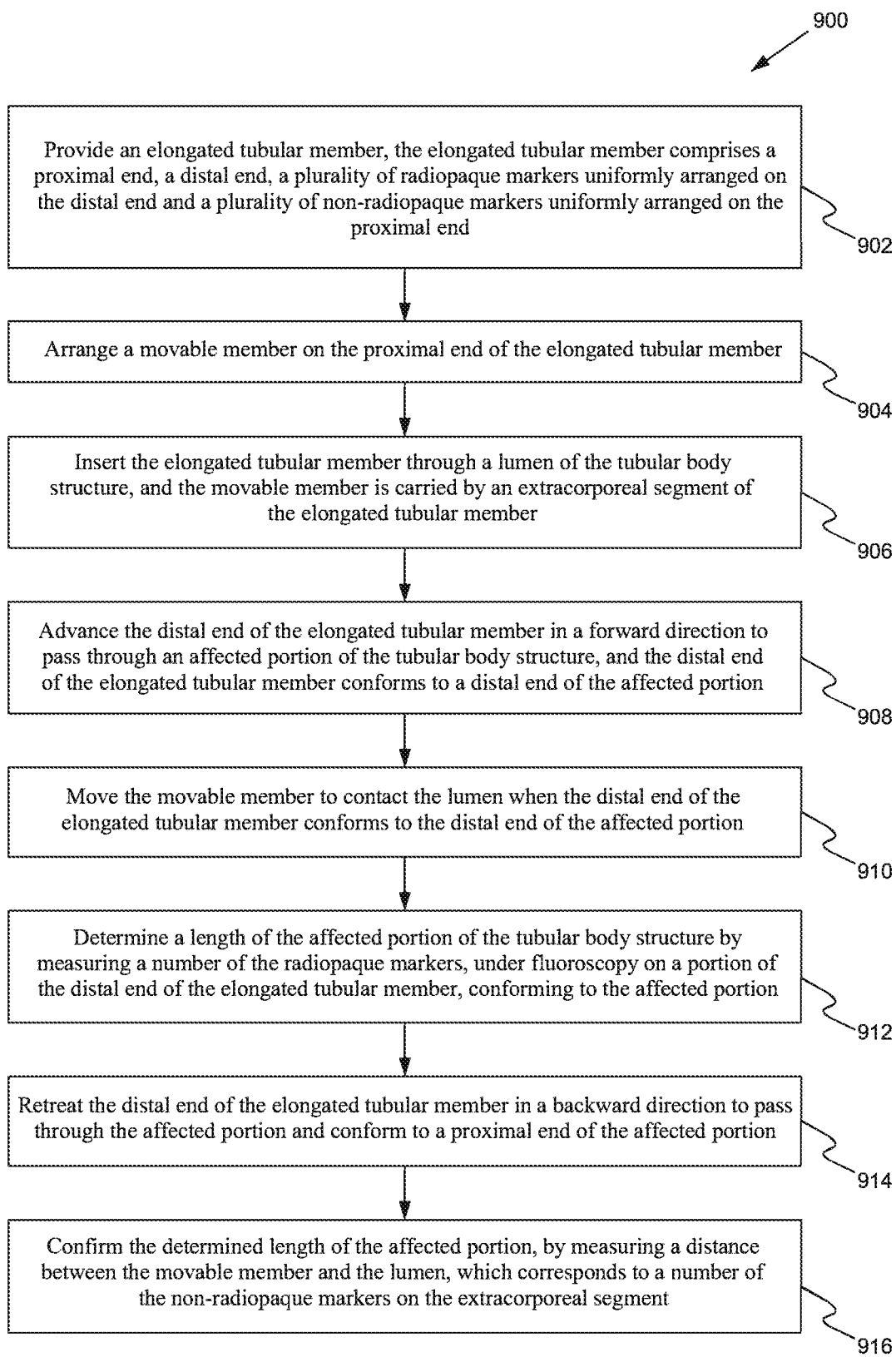
FIG. 9 is an illustration of steps of a method for measuring a length of a tubular body structure, in accordance with an example embodiment.

Referring to FIG. 9, illustrated are steps of a method 900 for measuring a length of a tubular body structure, in accordance with an embodiment of the present disclosure. Those skilled in the art would recognize that the method 900 is associated with the use of the devices 200-400, explained herein above in conjunction with FIGS. 2-8.

At step 902, an elongated tubular member is provided. The elongated tubular member comprises a proximal end, a distal end, a plurality of radiopaque markers uniformly arranged on the distal end and a plurality of non-radiopaque markers uniformly arranged on the proximal end.

At step 904, a movable member is arranged on the proximal end of the elongated tubular member.

At step 906, the elongated tubular member is inserted through a skin entry site of the tubular body structure (typically over a guidewire), and the movable member is carried by an extracorporeal segment of the elongated tubular member.

At step 908, the distal end of the elongated tubular member is advanced in a forward direction to pass through an affected portion of the tubular body structure, and the distal end of the elongated tubular member conforms to a distal end of the affected portion.

At step 910, the movable member is moved to contact the skin entry site (or guide sheath or guide catheter) when the distal end of the elongated tubular member conforms to the distal end of the affected portion.

At step 912, a length of the affected portion is determined of the tubular body structure by measuring a number of the radiopaque markers, under fluoroscopy on a portion of the distal end of the elongated tubular member, conforming to the affected portion.

At step 914, the distal end of the elongated tubular member is retreated in a backward direction to pass through the affected portion and conform to a proximal end of the affected portion.

At step 916, the determined length of the affected portion is confirmed, by measuring the distance between the movable member and the skin entry site. This may be done by, in an embodiment, by visual estimation of the number of non-radiopaque markers spanning length D between the moveable member and the skin entry site. In other embodiments this may be done by utilizing the retractable/moveable elements 512 on the moveable member 502, etc.

The steps 902 to 914 are only illustrative and other alternatives can also be provided where one or more steps are added, one or more steps are removed, or one or more steps are provided in a different sequence without departing from the scope of the claims herein. For example, in the method, the elongated tubular member also includes a guiding head member, having radiopaque markers, coupled to the distal end of the elongated tubular member. Further, a guide wire is configured to be received through the elongated tubular member and extends out from the distal end. Moreover, in the method 900, the elongated tubular member may be a mono-rail catheter or an over-the-wire catheter depending on the embodiment.

Embodiments of the present disclosure substantially eliminate or at least partially address the aforementioned problems in the background, and enable precise length measurement of tubular body structures for medical procedures. The present disclosure describes an inexpensive, quick, simple and intuitive mechanism of making precise length measurements during interventional procedures. Specifically, the present disclosure involves two different independent techniques for providing improved accuracy for the length measurements. For example, the length may be measured using radiopaque markers (aligning with an affected portion) under fluoroscopy, and the measured length may be authenticated (confirmed) by measuring (or counting) non-radiopaque markers on the extracorporeal segment using the length measuring arrangement. Also, the device of present disclosure does not impede the flow of interventional procedures, and does not require an operator to use unfamiliar equipment. In comparison to quantitative coronary angiography, the present disclosure does not require expensive software or modifications to angiographic equipment, and is not subject to the inaccuracies caused by projection of complex 3-dimensional structures into a 2-dimensional image. Further, in contrast to use of a marker guide wire, with the present disclosure the physician can use any guide wire of his or her choice, and without being distracted by the radiographic markers of the guide wire. Moreover, in comparison to an over-the-wire marker catheter, the present disclosure includes all the advantages of a mono-rail catheter. Additionally, in reference to monorail or over-the-wire catheters specified above, the present disclosure may have functionality of diagnostic catheters, balloon catheters, stent catheters, fractional flow reserve catheters, intravascular ultrasound catheters, mechanical or rheolytic thrombectomy catheters, optical coherence tomography catheters, atherectomy catheters, drainage catheters, or perfusion catheters. Finally, the embodiments of the present disclosure may use wires with additional functionality such as guide wire, fractional flow reserve wire, coronary flow reserve wire, recanalizing wire or pacing wire.

The embodiments illustrated and described herein as well as embodiments not specifically described herein but within the scope of aspects of the invention constitute exemplary system means for measuring length of a tubular body structure.

The benefits and advantages described above may relate to one embodiment or may relate to several embodiments. The embodiments are not limited to those that solve any or all of the stated problems or those that have any or all of the stated benefits and advantages.

The operations of the method described herein may be carried out in any suitable order, or simultaneously where appropriate. Additionally, individual blocks may be added or deleted from any of the methods without departing from the spirit and scope of the subject matter described herein. Aspects of any of the examples described above may be combined with aspects of any of the other examples described to form further examples without losing the effect sought.

The above description is given by way of example only and various modifications may be made by those skilled in the art. The above specification, examples and data provide a complete description of the structure and use of exemplary embodiments. Although various embodiments have been described above with a certain degree of particularity, or with reference to one or more individual embodiments, those skilled in the art could make numerous alterations to the disclosed embodiments without departing from the spirit or scope of this specification.

What is claimed is:

1. A device for measuring a length of a tubular body structure, the device comprising:
   an elongated tubular member having a proximal end and a distal end, the elongated tubular member comprising:
   a plurality of radiopaque markers uniformly arranged on the distal end and a plurality of non-radiopaque markers uniformly arranged on the proximal end, and a guiding head member coupled to the distal end of the elongated tubular member, wherein a number of the radiopaque markers of a portion of the distal end of the elongated tubular member conforming to an affected portion of the tubular body structure enables in measuring a length of the affected portion, when the elongated tubular member is inserted through a skin entry site of the tubular body structure under fluoroscopy; and
   a length measuring arrangement mounted on the proximal end of the elongated tubular member, the length measuring arrangement comprising a movable member, wherein the movable member comprises of a hinge and at least one channel, the at least one channel extending along the length of the movable member.

2. The device as claimed in claim 1, wherein a number of the non-radiopaque markers of the proximal end on an extracorporeal segment of the elongated tubular member enables in measuring and authenticating the measured length of the affected portion of the tubular body structure.

3. The device as claimed in claim 1,
   wherein a distance between the skin entry site of the tubular body structure and the movable member on an extracorporeal segment of the elongated tubular member enables in measuring and authenticating the measured length of the affected portion of the tubular body structure.

4. The device as claimed in claim 1, wherein the length measuring arrangement further comprises:
   a sensor responsive to the non-radiopaque markers; and
   a processor communicably coupled to the sensor,
   wherein the sensor and the processor are arranged on the movable member, and the sensor senses the number of the non-radiopaque markers and the processor measures the length of the affected portion of the tubular body structure by measuring a distance based on the sensed number of the non-radiopaque markers on the extracorporeal segment.

5. The device as claimed in claim 4, wherein in use,
   the elongated tubular member is configured to be inserted through the skin entry site of the tubular body structure and the movable member is carried by the extracorporeal segment of the elongated tubular member,
   the guiding head member is configured to pass through the affected portion of the tubular body structure in a forward direction to conform to a distal end of the affected portion,
   the movable member is moved to contact the skin entry site of the tubular body structure when the guiding head member conforms to the distal end of the affected portion,
   the movable member is retained in a fixed position and the guiding head member is retreated in a backward direction to pass through the affected portion and conform to a proximal end of the affected portion, and
   the distance between the movable member and the skin entry site is determined to measure the length of the affected portion of the tubular body structure, wherein the distance between the movable member and the skin entry site corresponds to a distance between the distal end and the proximal end of the affected portion.

6. The device as claimed in claim 4, wherein the movable member comprises:
   a first movable part; and
   a second movable part.

7. The device as claimed in claim 4, wherein the movable member is cylindrical piece having the at least one channel conforming to a diameter of the elongated tubular member to receive the elongated tubular member there-through.

8. The device as claimed in claim 4, wherein the movable member is removably mounted on the proximal end of the elongated tubular member.

9. The device as claimed in claim 4, wherein the movable member is snap-fitted on the proximal end of the elongated tubular member.

10. The device as claimed in claim 4, wherein the movable member is threadably or slideably mounted on the proximal end of the elongated tubular member.

11. The device as claimed in claim 4, wherein the elongated tubular member is configured to accommodate a guide wire, which is adapted to be received through the proximal end of the elongated tubular member and extend out of the guiding head member.

12. The device as claimed in claim 11, wherein the elongated tubular member is an over-the-wire catheter.

13. The device as claimed in claim 4, further comprising a guide wire adapted to be received through the elongated tubular member from adjacent to the distal end and extends out from the distal end.

14. The device as claimed in claim 13, wherein the elongated tubular member is a monorail catheter, and the guide wire is configured to be received through the at least one channel in the movable member.

15. A length measuring arrangement for a tubular body structure, the length measuring arrangement being adapted to be mounted on an elongated tubular member having a proximal end, a distal end, a plurality of radiopaque markers uniformly arranged on the distal end, and a plurality of non-radiopaque markers uniformly arranged on the proximal end, the length measuring arrangement comprising:
  a movable member adapted to be arranged on the proximal end of the elongated tubular member, the movable member comprising a hinge and at least one channel extending along the length of the movable member and conforming to diameter of the elongated tubular member to receive the elongated tubular member therethrough;
  a sensor responsive to the non-radiopaque markers; and
  a processor communicably coupled to the sensor;
wherein the sensor and the processor are arranged on the movable member, and the sensor senses a number of the non-radiopaque markers on an extracorporeal segment of the elongated tubular member and the processor measures a length of an affected portion of the tubular body structure based on the sensed number of the non-radiopaque markers.

16. The length measuring arrangement as claimed in claim 15, wherein in use,
  the elongated tubular member are configured to be inserted through a skin entry site of the tubular body structure and the movable member is carried by the extracorporeal segment of the elongated tubular member,
  the distal end of the elongated tubular member is configured to pass through the affected portion of the tubular body structure in a forward direction to conform to a distal end of the affected portion,
  the movable member is moved to contact the skin entry site of the tubular body structure when the distal end of the elongated tubular member conforms to the distal end of the affected portion,
  the movable member is retained in a fixed position and the distal end of the elongated tubular member is retreated in a backward direction to pass through the affected portion and conform to a proximal end of the affected portion, and
  the distance between the movable member and the skin entry site is determined to measure the length of the affected portion of the tubular body structure, wherein the distance between the movable member and the skin entry site corresponds to a distance between the distal and proximal ends of the affected portion.

17. The length measuring arrangement as claimed in claim 16, wherein a guide wire is configured to be received through the elongated tubular member from adjacent to the distal end and extends out from the distal end.

18. The length measuring arrangement as claimed in claim 17, wherein the elongated tubular member is a mono-rail catheter, and the guide wire is configured to be received through the at least one channel in the movable member.

19. The length measuring arrangement as claimed in claim 15, wherein the elongated tubular member further comprises a guiding head member coupled to the distal end of the elongated tubular member.

20. The length measuring arrangement as claimed in claim 15, wherein a guide wire is adapted to be received through the proximal end of the elongated tubular member and extend out of the guiding head member.

21. The length measuring arrangement as claimed in claim 20, wherein the elongated tubular member is an over-the-wire catheter.

22. A method for measuring a length of a tubular body structure, the method comprising:
  providing an elongated tubular member, the elongated tubular member comprising a proximal end, a distal end, a plurality of radiopaque markers uniformly arranged on the distal end and a plurality of non-radiopaque markers uniformly arranged on the proximal end;
  arranging a movable member on the proximal end of the elongated tubular member, the movable member comprising a hinge and at least one channel extending along the length of the movable member;
  inserting the elongated tubular member through a skin entry site of the tubular body structure, wherein the movable member is carried by an extracorporeal segment of the elongated tubular member;
  advancing the distal end of the elongated tubular member in a forward direction to pass through an affected portion of the tubular body structure, wherein the distal end of the elongated tubular member conforms to a distal end of the affected portion;
  moving the movable member to contact the skin entry site when the distal end of the elongated tubular member conforms to the distal end of the affected portion;
  determining a length of the affected portion of the tubular body structure by measuring a number of the radiopaque markers, under fluoroscopy on a portion of the distal end of the elongated tubular member, conforming to the affected portion;
  retreating the distal end of the elongated tubular member in a backward direction to pass through the affected portion and conform to a proximal end of the affected portion; and
  confirming the determined length of the affected portion, by measuring a distance between the movable member and the skin entry site, which corresponds to a number of the non-radiopaque markers on the extracorporeal segment.

23. The method as claimed in claim 22, wherein the elongated tubular member further comprises a guiding head member coupled to the distal end of the elongated tubular member.

24. The method as claimed in claim 22, wherein a guide wire is adapted to be received through the proximal end of the elongated tubular member and extend out of the guiding head member.

25. The method as claimed in claim 24, wherein the elongated tubular member is an over-the-wire catheter.

26. The method as claimed in claim 22, wherein a guide wire is configured to be received through the elongated tubular member from adjacent to the distal end and extends out from the distal end.

27. The method as claimed in claim 26, wherein the elongated tubular member is a mono-rail catheter, and the guide wire is configured to be received through the at least one channel in the movable member.

\* \* \* \* \*